(12) United States Patent
Shirasaki

(10) Patent No.: US 6,805,670 B2
(45) Date of Patent: Oct. 19, 2004

(54) ELECTRONIC BLOOD PRESSURE MONITOR

(75) Inventor: Osamu Shirasaki, Kyoto (JP)

(73) Assignee: Omron Corporation, Kyoto (JP)

( * ) Notice: Subject to any disclaimer, the term of this patent is extended or adjusted under 35 U.S.C. 154(b) by 87 days.

(21) Appl. No.: 10/361,018

(22) Filed: Feb. 10, 2003

(65) Prior Publication Data

US 2003/0181816 A1 Sep. 25, 2003

(30) Foreign Application Priority Data

Feb. 28, 2002 (JP) .......................................... 2002-053671

(51) Int. Cl.$^7$ ................................................ A61B 5/02
(52) U.S. Cl. .................... 600/490; 600/493; 600/494; 600/500
(58) Field of Search ................................ 600/485, 490, 600/492–496, 500–503

(56) References Cited

U.S. PATENT DOCUMENTS

| | | | | |
|---|---|---|---|---|
| 4,830,019 A | * | 5/1989 | Shirasaki et al. | ........... 600/494 |
| 5,094,245 A | * | 3/1992 | Shirasaki | .................... 600/493 |
| 5,156,158 A | * | 10/1992 | Shirasaki | .................... 600/493 |
| 5,323,782 A | * | 6/1994 | Shirasaki et al. | ........... 600/493 |
| 6,582,374 B2 | * | 6/2003 | Yokozeki | .................... 600/494 |
| 6,602,198 B2 | * | 8/2003 | Yokozeki | .................... 600/485 |

* cited by examiner

*Primary Examiner*—Mary Beth Jones
*Assistant Examiner*—Navin Natnithithadha
(74) *Attorney, Agent, or Firm*—Morrison & Foerster LLP

(57) ABSTRACT

Provided is an electronic blood pressure monitor capable of realizing functions of blood pressure measurement in a shorter time and blood pressure measurement with more of correctness in the same and one construction thereof. The electronic blood pressure monitor includes: an oscillometric measuring section capable of calculating a blood pressure with a high precision using much of biogenic information though a time is required since a blood pressure is calculated during a period in which the cuff pressure is gradually changed; and an SPD measuring section completing measurement in a short time though a fluctuation in precision of measurement arises according to an with less of biogenic information since individual difference a blood pressure is calculated using only one or several pulse waves. Since the oscillometric measuring portion performs a calibration processing for the SPD measuring section simultaneously during measurement thereof, calibrating operation a complicated can be practically excluded.

10 Claims, 12 Drawing Sheets

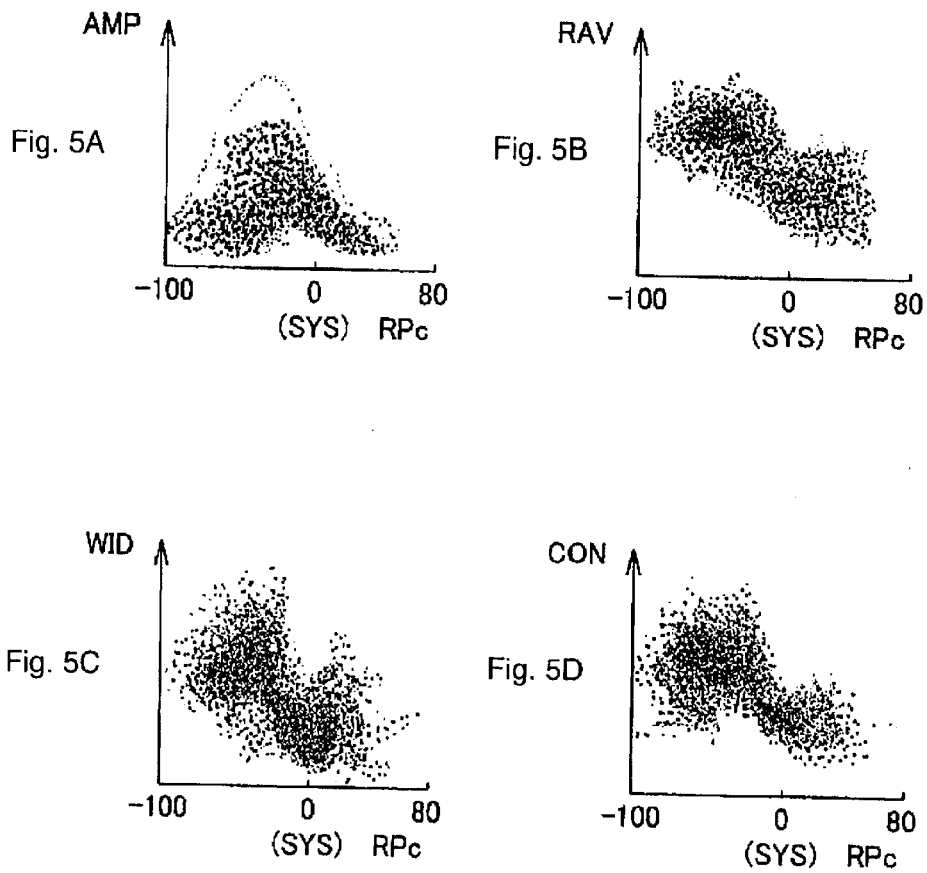
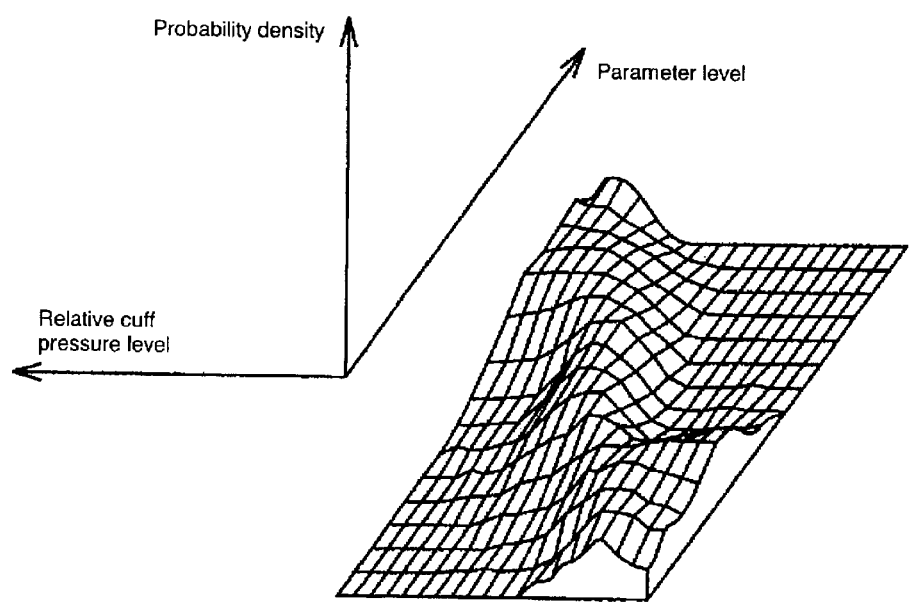
Fig. 6

Fig. 9A

| | First pulse wave | Second pulse wave | Third pulse wave | ... | ith pulse wave | ... | nth pulse wave |
|---|---|---|---|---|---|---|---|
| | P1(1) | P1(2) | P1(3) | ... | P1(i) | ... | P1(N) |
| | P2(1) | P2(2) | P2(3) | ... | P2(i) | ... | P2(N) |
| | P3(1) | P3(2) | P3(3) | ... | P3(i) | ... | P3(N) |
| | P4(1) | P4(2) | P4(3) | ... | P4(i) | ... | P4(N) |
| | Pc(1) | Pc(2) | Pc(3) | ... | Pc(i) | ... | Pc(N) |

| | First pulse wave | Second pulse wave | Third pulse wave | ... | ith pulse wave | ... | nth pulse wave |
|---|---|---|---|---|---|---|---|
| | P1(1) | P1(2) | P1(3) | ... | P1(i) | ... | P1(N) |
| | P2(1) | P2(2) | P2(3) | ... | P2(i) | ... | P2(N) |
| | P3(1) | P3(2) | P3(3) | ... | P3(i) | ... | P3(N) |
| | P4(1) | P4(2) | P4(3) | ... | P4(i) | ... | P4(N) |
| | RPc(1) | RPc(2) | RPc(3) | ... | RPc(i) | ... | RPc(N) |

TB

ELECTRONIC BLOOD PRESSURE MONITOR

BACKGROUND OF THE INVENTION

1. Field of the Invention

The present invention relates to an electronic blood pressure monitor, and more particularly to an electronic blood pressure monitor using a pressurizing section (hereinafter referred to as a "cuff") for pressurizing a portion in one of four limbs and others of a mammal by injecting a fluid such as air thereinto.

2. Description of the Background Art

Among methods measuring a blood pressure using a cuff, there has been available a method in which various kinds of arterial signals (hereinafter referred to as "pulse waves") originated from changes in inner volume of an artery around which a pressure is applied with the cuff are captured in the course during which a pressure in the cuff (hereinafter referred to as a "cuff pressure") is gradually changed to calculate and determine a blood pressure based on the captured pulse waves. This method is called an oscillometric method.

FIG. 14 is a diagram showing a construction of an electronic blood pressure monitor that is applied to an example in a prior art practice and embodiments of the present invention. The electronic blood pressure monitor of FIG. 14 includes: a microprocessor 1 having, therein, a CPU (an abbreviation of a central processing unit) 1A for intensively controlling and monitoring the electronic blood pressure monitor itself as a center and a memory 1B; a cuff 2, being placed at a predetermined portion of a mammal in order to pressurize an artery; a gradual pressure reduction section 3, a rapid discharging section 4, a pressurizing section 5 and a cuff pressure detecting section 6 all of which are connected to the cuff 2 by an air system; a pulse wave detecting section 7 detecting a pulse wave originating from a change in volume of the artery produced in the course during which the artery is pressurized with the cuff 2; an amplifying circuit-AD (analog-digital) converters 8 and 9; an input interface 10 and an output interface 11. A pressure inside the cuff 2 is controlled by the gradual pressure reduction section 3, the rapid discharging section 4 and the pressurizing section 5.

The CPU 1A of the microprocessor 1 controls other sections. The pressurizing section 5 has a pressure pump, by which the cuff 2 is pressurized to a predetermined cuff pressure. The gradual pressure reduction section 3 has a valve for reducing a cuff pressure. While the valve is closed during pressurization of the cuff 2, it works so as to gradually reduce a cuff pressure when being opened. The rapid discharging section 4 has a valve for reducing a cuff pressure. While the valve is closed during pressurization of the cuff 2, it works so as to rapidly reduce a cuff pressure when being opened. The cuff pressure detecting section 6 has a pressure sensor to detect a cuff pressure. The pulse wave detecting section 7 detects a pulse wave. The amplifying circuit-AD converters 8 and 9 amplify signals outputted from the cuff pressure detecting section 6 and the pulse wave detecting section 7, respectively, to convert the signals to digital values and to give the digital values to the microprocessor 1. The microprocessor 1 processes given data to calculate a blood pressure value and to output a result of the calculation through the output interface 11. The input interface 10 is constituted of switches, buttons and others and installed so as to enable to be externally operable by a user. The output interface 11 is constituted of a display section for displaying information; a printer for printing the information; a speech output section for outputting the information in speech; and others.

A pulse wave is produced by a change in inner volume of an arterial blood vessel, around which an external pressure (a cuff pressure) is applied by pressurization of the cuff 2, due to a balance between the cuff pressure and an pulsating inner pressure (blood pressure). In an oscillometric method, a blood pressure value (at least one of a systolic blood pressure, a diastolic blood pressure and an average blood pressure) is calculated from a pattern of changes in amplitude of pulse waves corresponding to chronological levels of a cuff pressure that changes in the course during which the cuff pressure increases or decreases gradually, for example, stepwise or continuously in a range between a value in the vicinity of a systolic blood pressure (a so-called maximum blood pressure) and a value in the vicinity of a diastolic blood pressure (a so-called minimum blood pressure).

In this method, though a necessity arises for raising a pressure inside the cuff 2 to a value equal to or higher than a systolic blood pressure at the first stage, the systolic blood pressure largely alters according to an individual difference or various factors of the same individual as well, so pressurization has been started after adjusting a pressurization amount given by the pressurizing section 5 in the cuff 5 with an change-over switch provided to the input interface 10. Contradiction arises, however, in adjustment of the pressurization amount performed based on in-advance estimation of a user in an electronic blood pressure monitor with which the user measures a blood pressure since the user uses the electronic blood pressure monitor to measure a blood pressure unknown to the user and such operation has actually been tough to the user.

Therefore, a method has been contrived in which a pulse wave is detected during pressurization of the pressurizing section 5 in the cuff 2 to estimate a systolic blood pressure with a certain precision and to cease pressurization in the cuff 2 at an optimal level based on the estimation. This method is called an automatic pressure setting function and disclosed in JP patents No. 2842696, No. 2936814, No. 2936816, No. 3008582, No. 3042051 and No. 3042052. With the method adopted, a necessity has been removed for a manual operation of a user to adjust a pressurization value through estimation of a systolic blood pressure.

In an oscillometric method, however, since there is still a necessity for gradually reducing a cuff pressure down to a comparative low pressure equal to or lower than a diastolic blood pressure from a high pressure higher than a systolic blood pressure, not only has a user been placed under a restraint in a blood pressure measurement for a long time, which is troublesome to the user, but a problem has also arisen that an environment of usage is restricted and a rapid change in blood pressure cannot be captured though a precision of measurement has become high due to acquirement of information for measuring a blood pressure over a long time, that is to say, due to acquirement of much biogenic information. That is to say, a time is consumed in measurement in the oscillometric method for the reason that a cuff pressure cannot be reduced at a high speed in order to maintain a precision.

In contrast thereto, another method has been proposed in which a measuring time can be shortened even though the measuring method still uses the cuff 2. For simplicity of description of the method, the method is herein called an SPD method (Single Pulse Determination). The SPD method is disclosed in JP patent No. 2745467, No. 2855767 and others. According to an SPD method, a cuff pressure is raised to an arbitrary value to maintain there and a pulse wave signal is captured by one wave or several waves, thereby enabling estimation of a blood pressure value. A construction of an electronic blood pressure monitor to which an SPD method is applied is almost similar to that shown in FIG. 14 only with the exception that no necessity arises for the gradual pressure reduction section 3.

An SPD method uses a change in a waveform of a pulse wave depending on a value of a cuff pressure relative to a blood pressure (hereinafter referred to as a "relative cuff pressure"). To briefly describe a principle thereof, a cuff pressure is at first raised to an arbitrary value to then capture at least one pulse wave and to obtain a waveform characteristic amount of the pulse wave. The term, a waveform characteristic amount, is one obtained by quantifying characteristics of a waveform of a wave pulse. Then, a wave form characteristic amount is compared with a predetermined function defining a relationship between a relative cuff pressure and a waveform characteristic amount of a pulse wave to estimate a relative cuff pressure at the time when the pulse wave is captured. Finally, a value of the estimated relative cuff pressure is subtracted from a known cuff pressure (hereinafter referred to as an absolute cuff pressure) detected by the cuff pressure detecting section 6 at the time when the pulse wave was captured; thereby estimating a blood pressure.

According to an SPD method, in such a way, changes in pulse waves (changes in amplitude) are not captured while a cuff pressure is altered over a wide range as done in an oscillometric method but a blood pressure is estimated from the absolute value of a waveform characteristic amount of one pulse wave, thereby, enabling calculation of a blood pressure value from one pulse wave according to the principle. Therefore, since a necessity arises only for a very short time length during which a user is placed under restraint in measurement of a blood pressure, advantages are attained that detection of even a rapid change in blood pressure can be achieved, measurement can be done at anytime and anywhere without selecting an environment of usage and the measurement is comfortable without a pain accompanied therewith. An SPD method, however, is very much reduced in measuring time, but contrary to this, a case has arisen where a precision is insufficient for a particular user since a blood pressure is determined from less of biogenic information and an individual difference is present in a relationship between a relative cuff pressure and a waveform characteristic amount.

In this way, since blood pressure measurements of an oscillometric method and an SPD method have respective characteristics conflicting with each other, a desire has been arisen that a user selectively uses one of the measuring methods according to a situation such as a time, a place or the like. That is to say, there has been a desire of selective use of the methods according to a situation that a user at work measures a blood pressure in a short time period with a blood pressure measurement of a SPD method but the user at home measures a blood pressure in an enough time that is allowed to spend with a good precision using an oscillometric method. However, since there have not been available an electronic blood pressure monitor having both functions of blood pressure measurement of an oscillometric method and an SPD method, a user has had to purchase electronic blood pressure monitors of an oscillometric method and an SPD method, which negates an economy.

Furthermore, though an SPD method is very much reduced in measuring time, a case has been encountered where a precision is not sufficient for a need of a particular user, so a necessity has been arisen for adjusting a relationship between a relative cuff pressure and a waveform characteristic amount with information showing characteristics of a pulse wave different according to an individual to calibrate a result of measurement in an application requiring a high precision. The information used for calibration of a result of measurement is hereinafter referred to as calibration information. In other words, both of electronic blood pressure monitors of a SPD method and a prior art electronic blood pressure monitor are both operated, separately purchasing an electronic blood pressure monitor in the prior art (for example, an electronic blood pressure monitor according to an oscillometric method) for use in calibration to obtain calibration information when a precision is required, and a value of the prior art electronic blood pressure monitor, that is to say, calibration information, has to be inputted to an electronic blood pressure monitor of an SPD method, having lead to requirement of a complicated operation.

Though an SPD method can calculate a blood pressure in a procedure in which the cuff 2 is pressurized to an arbitrary value to capture at least one pulse wave under the pressure from the principle thereof, a pulse wave transmitted from a mammal is very weak in a case where a pressurization value is raised to a value excessively larger than a blood pressure, which increases a noise component in a relatively large value, that is to say, deteriorates an S/N ratio, to disable a waveform characteristic amount of a pulse wave to be correctly calculated, having also resulted in a problem to produce a large error.

SUMMARY OF THE INVENTION

Therefore, it is an object of the present invention to provide an electronic blood pressure monitor capable of performing measurement of a blood pressure in a shorter time and with more of correctness.

It is another object of the present invention to provide an electronic blood pressure monitor capable of realizing functions of blood pressure measurement in a shorter time and blood pressure measurement with more of correctness in the same and one construction thereof.

An electronic blood pressure monitor according to an aspect of the present invention includes a cuff configured to be mounted on a predetermined portion of a subject for pressurizing an artery of the subject, a cuff pressure controller for controlling a cuff pressure inside the cuff, a pressure detector for detecting the cuff pressure, a pulse wave detector for detecting a pulse wave of the artery that is pressurized by the cuff, and a first blood pressure measuring portion and a second blood measuring portion being selectively used by the electronic blood pressure monitor at a time.

The first blood pressure measuring portion includes a first blood pressure calculation unit and a calibration unit for calibrating the second blood pressure measuring portion. The first blood pressure calculating unit calculates and outputs a blood pressure of the subject based on a set of cuff pressures chronologically detected by the pressure detector during a period in which the cuff pressure is gradually changed by the cuff pressure controller and on amplitudes of the pulse waves detected by the pulse wave detector at the timings of the corresponding cuff pressure detection by the pressure detector.

The second blood pressure measuring portion includes a parameter measuring unit, a function memory, a function selection unit and a second blood pressure calculating unit.

The parameter measuring unit provides a measured value of pulse wave parameter based on at least one of the pulse waves detected by the pulse wave detector, the pulse wave parameter being indicative of a waveform of the pulse wave that represents a relative cuff pressure corresponding to a pressure difference between the detected cuff pressure and the blood pressure of the subject.

The function memory stores a function of the relative cuff pressure including a set of sub-functions.

A function selection unit selects one of the sub-functions that corresponds to a level of the measured value of the pulse wave parameter.

A second calculating unit identifies the relative cuff pressure based on the selected sub-function and calculates the blood pressure of the subject subtracting the identified relative cuff pressure from the cuff pressure detected by the pressure detector at the time of the pulse wave detection.

The calibration unit includes a data gathering unit that gathers, for each of the pulse waves detected during an operation of the first blood pressure measuring portion at the timings of the corresponding cuff pressure detection, the corresponding relative cuff pressure and the corresponding measured value of the pulse wave parameter, and a data updating unit that modifies the function based on the relative cuff pressures and the corresponding measured values of the pulse wave parameter that are gathered by the data gathering unit.

Therefore, since the first blood pressure measuring portion further includes the calibration unit that calibrates the second blood pressure measuring portion, improvement can be realized on a precision of blood pressure measurement using the second blood pressure measuring portion that can measure a blood pressure in a shorter time while practically enabling exclusion of a complicated calibrating operation.

To practically enable exclusion of the calibrating operation means to complete calibration by the calibration unit during measurement of a blood pressure performed by a user in advance with the first blood pressure measuring portion, to be detailed. In other words, the data gathering unit gathers calibration information necessary for calibration of the second blood pressure measuring portion, that is to say, a blood pressure value calculated by the first blood pressure measuring portion at the time of blood pressure measurement, and pulse wave parameters (a characteristic amount) from one wave or several waves over a wide relative pressure range with the blood pressure value as a reference, and the data updating unit modifies values of functions corresponding to the pulse wave parameters in the function memory using the gathered relative cuff pressures and the corresponding values of the pulse wave parameters with respect to the pulse wave parameters; therefore, the user simply performs blood pressure measurement with the first blood pressure measuring portion without requiring any specific operation in addition.

Furthermore, an electronic blood pressure monitor includes: the first blood pressure measuring portion capable of calculating a blood pressure at a high precision using much of biogenic information though a time is required since a blood pressure is calculated during a period in which the cuff pressure is gradually changed; and a second blood pressure measuring portion completing measurement in a short time though a fluctuation in precision of measurement arises according to an individual difference with less of biogenic information since a blood pressure is calculated using at least one pulse wave.

Therefore, since blood measuring functions with respective different workings and characteristics are integrated in the same electronic blood pressure monitor, no necessity arises for separately purchasing blood pressure monitors with blood pressure measuring functions with respective different workings and characteristics, which is convenient and economical to a user.

Since the same electronic blood pressure monitor integrally has the two kinds of blood pressure measuring functions, different in operation and feature from each other in construction, a manufacturing cost of the equipment can be greatly reduced without a necessity for separate manufacture of two electronic blood pressure monitors.

Furthermore, if both functions are built in, for example, a microprocessor or the like in design and the measuring functions are selectively changed over therebetween by setting on a small scale, products with respective different functions working on different principles can also be manufactured in a single manufacture line.

According to another aspect of the present invention, an electronic blood pressure monitor is of a construction including: a cuff configured to be mounted on a predetermined portion of a subject for pressurizing an artery of the subject; a cuff pressure controller for controlling a cuff pressure inside the cuff; a pressure detector for detecting the cuff pressure; a pulse wave detector for detecting a pulse wave of the artery that is pressurized by the cuff and further includes a first blood pressure measuring portion and a second blood measuring portion being selectively used by the electronic blood pressure monitor at a time.

The first blood pressure measuring portion includes: a first blood pressure calculating unit. The first blood pressure calculating unit calculates and outputs a blood pressure of the subject based on a set of cuff pressures chronologically detected by the pressure detector during a period in which the cuff pressure is gradually changed by the cuff pressure controller and on amplitudes of the pulse waves detected by the pulse wave detector at the timings of the corresponding cuff pressure detection by the pressure detector.

The second blood pressure measuring portion includes: a parameter measuring unit; a function memory; and a function selection unit; and a second blood pressure calculating unit.

The parameter measuring unit provides a measured value of pulse wave parameter based on at least one of the pulse waves detected by the pulse wave detector, the pulse wave parameter being indicative of a waveform of the pulse wave that represents a relative cuff pressure corresponding to a pressure difference between the detected cuff pressure and the blood pressure of the subject.

The function memory stores a function of the relative cuff pressure including a set of sub-functions.

A function selection unit selects one of the sub-functions that corresponds to a level of the measured value of the pulse wave parameter.

A second calculating unit identifies the relative cuff pressure based on the selected sub-function and calculates the blood pressure of the subject subtracting the identified relative cuff pressure from the cuff pressure detected by the pressure detector at the time of the pulse wave detection.

In such a way, an electronic blood pressure monitor includes: the first blood pressure measuring portion capable of calculating a blood pressure at a high precision using much of biogenic information though a time is required since a blood pressure is calculated during a period in which the cuff pressure is gradually changed; and a second blood pressure measuring portion completing measurement in a short time though a fluctuation in precision of measurement arises according to an individual difference with less of biogenic information since a blood pressure is calculated using at least one pulse wave.

Therefore, since blood pressure measuring functions with respective different workings and characteristics are integrated in the same electronic blood pressure monitor, no necessity arises for separately purchasing blood pressure monitors with blood pressure measuring functions with respective different workings and characteristics, which is convenient and economical to a user.

Since the same electronic blood pressure monitor integrally has the two kinds of blood pressure measuring functions, different in operation and feature from each other in construction, a manufacturing cost of the equipment can be greatly reduced without a necessity for separate manufacture of two electronic blood pressure monitors.

Furthermore, if both functions are built in, for example, a microprocessor or the like in design and the measuring functions are selectively changed over therebetween by setting on a small scale, products with respective different functions working on different principles can also be manufactured in a single manufacture line.

BRIEF DESCRIPTION OF THE DRAWINGS

FIGS. 5A to 5D are graphs showing values of pulse wave parameters plotted using the abscissas on which a scale for a relative cuff pressure is calibrated;

FIG. 6 is diagram illustrating a probability density function calculated from a probability density distribution;

FIGS. 9A and 9B are representations showing tables filled out with 4 kinds of pulse wave parameters and values of an absolute cuff pressure for each of pulse waves;

DESCRIPTION OF THE PREFERRED EMBODIMENTS

Description will be given of embodiments of the present invention below with reference to the accompanying drawings. Note that while a pulse wave is detected based on the pulse waves (cuff pressure pulse waves) super imposing a cuff pressure signal, detection of a pulse wave has also been realized based on an optical or electrical principle other than a cuff pulse pressure pulse but no specific limitation is imposed thereto.

(First Embodiment)

In the first embodiment, a processing is performed that improves a precision of measurement in an SPD method based on information detected according to an oscillometric method. Description will be given of this processing in the order of a equipment construction of an electronic blood pressure monitor, an overall operation therein, operations in blood pressure measurement according to an oscillometric method, the principle of blood pressure measurement according to an SPD method, operations in blood pressure measurement of an SPD method according to this embodiment and the principle of calibration for an individual difference in an SPD method applied to this embodiment.

(Equipment Construction)

Figure 1:
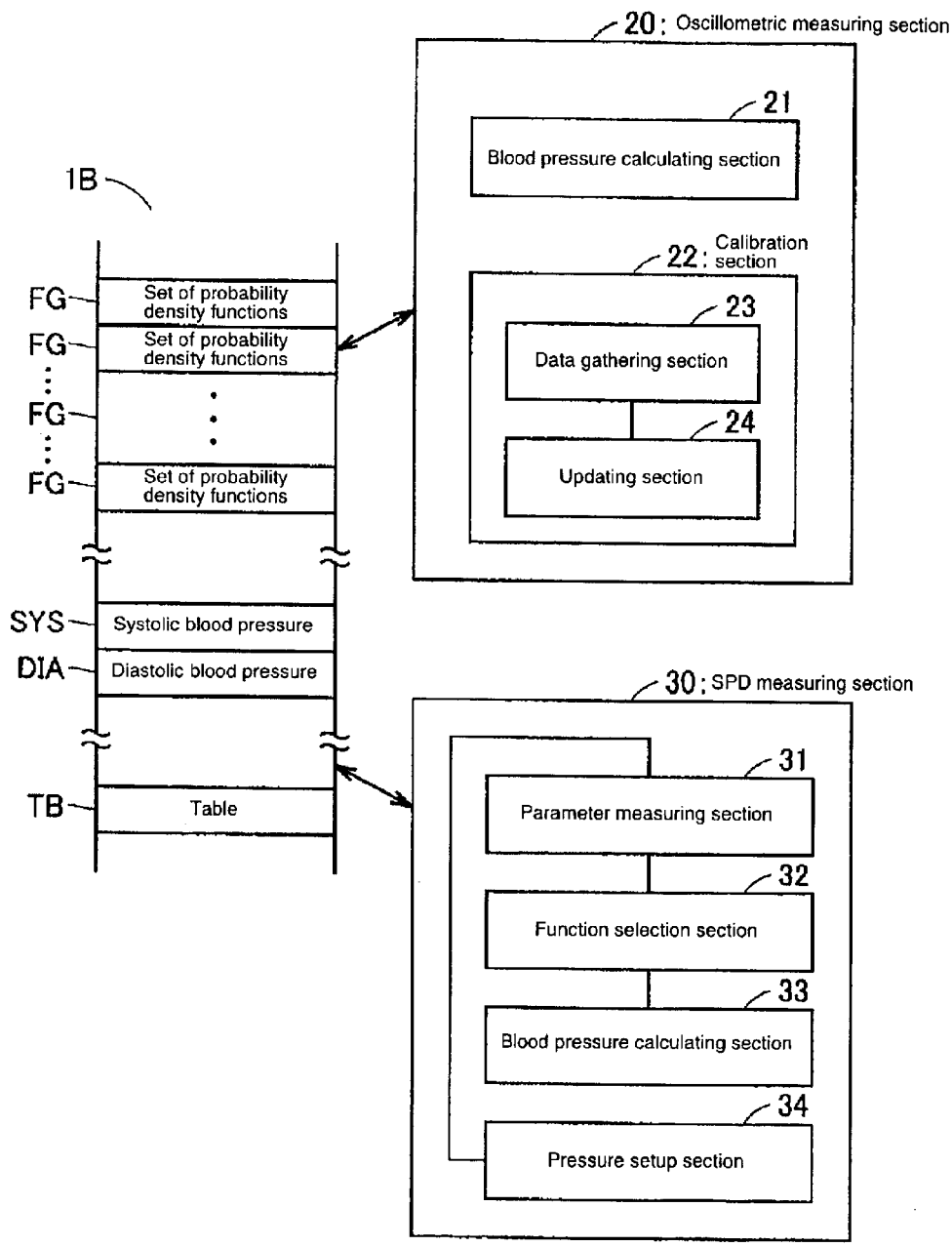
FIG. 1 is a diagram showing a function construction for electronic blood pressure measurement relating to respective embodiments.
Figure 14:
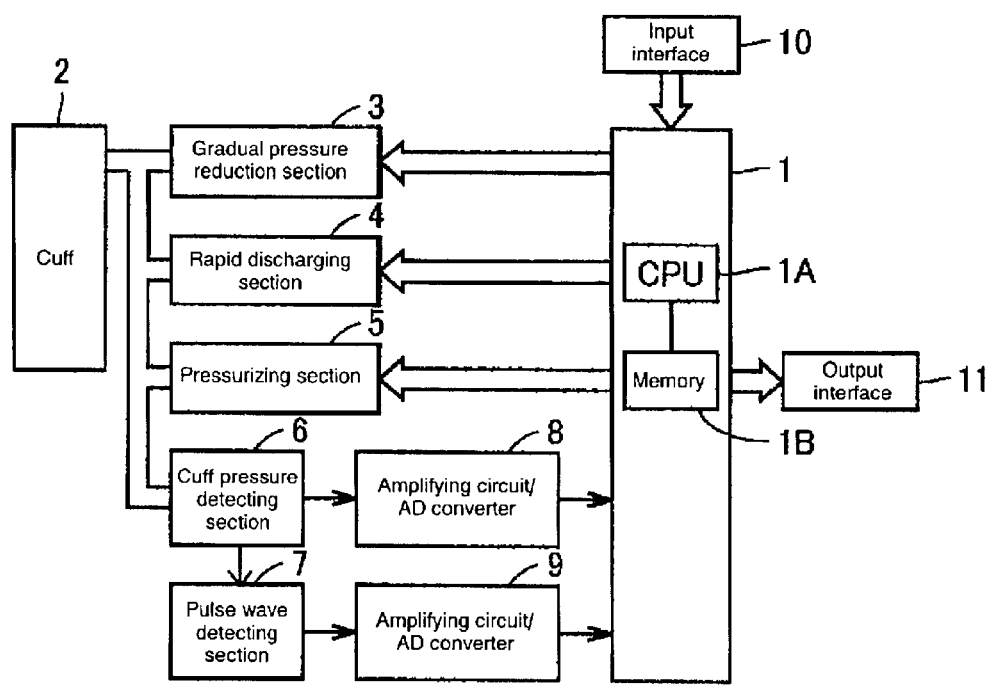
FIG. 14 is a diagram showing an equipment construction of an electronic blood pressure monitor that is applied to an example in a prior art practice and embodiments of the present invention.

No description is given of an equipment construction of each of electronic blood pressure monitors relating to the embodiments since the equipment construction is similar to that shown in FIG. 14. In FIG. 1, there is shown a function construction for electronic blood pressure measurement relating to the embodiments.

Referring to FIG. 1, an electronic blood pressure monitor includes: an oscillometric measuring section 20 measuring a blood pressure according to an oscillometric method performing a processing while referring to information stored in a memory 1B; and an SPD blood pressure measuring section 30 measuring a blood pressure according to a SPD method performing a processing while referring to information stored in the memory 1B. Included in information stored in the memory 1B are: plural probability density functions FG; and a table TB for storing, therein, a determined systolic blood pressure SYS and a determined diastolic blood pressure DIA, and calibration information. Since the determined systolic blood pressure SYS and the determined diastolic blood pressure DIA are used for a calibration processing in a SPD method, the pressures may be called calibration information.

The oscillometric measuring section 20 includes: a blood pressure calculating section 21 for measuring a blood pressure to calculate and a calibration section 22 for calibrating a precision of measurement in an SPD method. The calibration section 22 has therein an data gathering section 23 gathering calibration information; and an updating section 24 updating information referred to in the SPD method based on the gathered calibration information.

The SPD measuring section 30 includes: a parameter measuring section 31 providing parameters showing characteristics of a wave form of a measured pulse wave; a function selection section 32 selectively extracting corresponding functions based on measured values of the parameters provided; and a blood pressure calculating section 33 calculating a blood pressure using the selected functions; and a pressure set up section 34. The pressure set up section 34 determines a pressurization level of the cuff 2 in advance to actual measurement of a pulse wave by the parameter measuring section 31 so as to enable a pulse wave to be detected at an optimal cuff pressure to operate so as to pressurize the cuff 2 to the level.

Description will be given of details of the sections later.
(Overall Operation)

Figure 2:
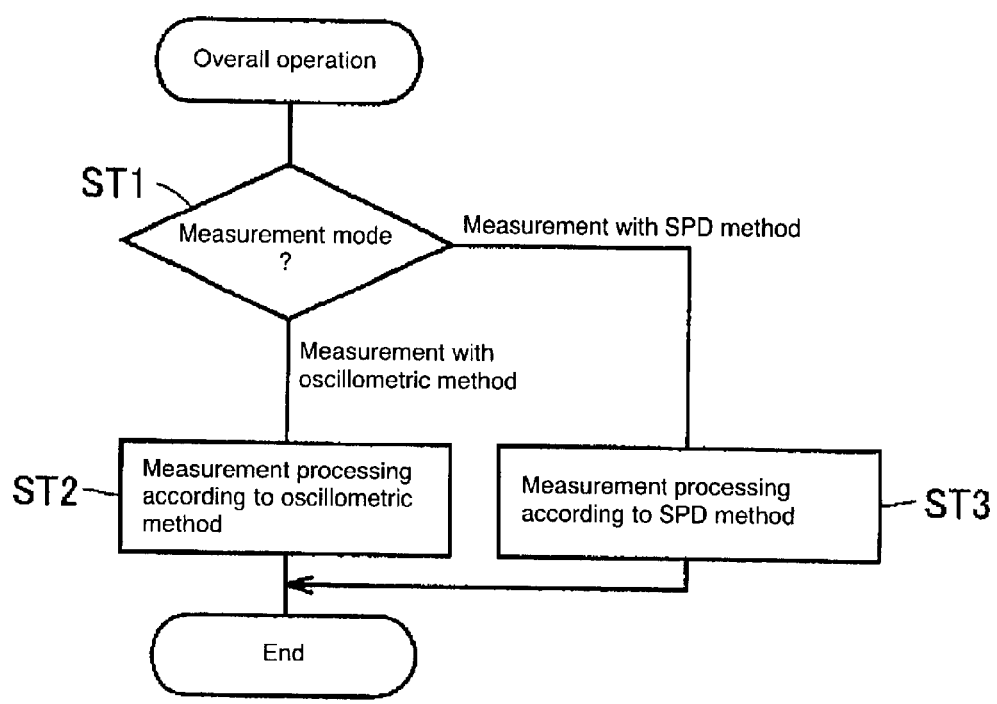
FIG. 2 is a flowchart showing an overall operation in an electronic blood pressure monitor relating to a first embodiment.

FIG. 2 is a flowchart showing an overall operation in an electronic blood pressure monitor relating to this embodiment. Herein, a systolic blood pressure and a diastolic blood pressure, both estimated, are called a systolic blood pressure SP and a diastolic blood pressure DP. The finally determined systolic blood pressure and diastolic blood pressure are called a systolic blood pressure SYS and diastolic blood pressure DIA, respectively. A user can select one of measurement modes of an oscillometric method and an SPD method by a switch operation in the input interface 10.

Referring to FIG. 2, the CPU 1A at first determines which of measurement modes is selected, an oscillometric method or an SPD method based on the switch operation in the input interface 10 by the user or the like (ST1). When the oscillometric method is selected, a blood pressure measurement processing according to the oscillometric method is performed by the oscillometric measuring section 20 (ST2), while when the SPD method is selected, a blood pressure measurement processing according to the SPD method is performed by the SPD measuring section 30 (ST3) to end the measurement operations after performing them in both of the cases. Description will be given of the two blood pressure measurement processings later.

Though not shown in FIG. 2, a calibration processing is performed by the calibration section 22 during the blood pressure measurement processing in the oscillometric method based on calibration information of an individual for improving a precision of measurement in the SPD method. In other words, the data gathering section 23 sequentially stores a waveform characteristic amount of each pulse wave and a cuff pressure as calibration information showing up during the measurement operation of a blood pressure in the oscillometric method into the table TB of the memory 1B and the updating section 24 performs a calibration processing based on calibration information of stored contents.

The calibration processing used herein means in particular to process characteristics, that is a waveform characteristic amount, of a waveform of a pulse wave of a user as an individual obtained by an oscillometric method so as to be able to be reflected in an algorithm for measurement of a blood pressure according to an SPD method. Therefore, when the calibration processing is performed, a precision of measurement is improved even in a SPD method since measurement according to characteristics of a pulse wave of an individual is enabled.

Herein, since characteristics of a pulse wave are altered by various kinds of factors, for example, by variations in physiologic conditions and others accompanied with a seasonal fluctuation, progress in illness or recovery therefrom, or variation of physiological conditions due to administration of medicine, even for a user as a particular individual, it is desirable to use the latest calibration information at all times in calibration processing. Therefore, it is desirable that a calibration processing is repeatedly performed based on new calibration information each time when a predetermined time elapses.

In this embodiment, therefore, for example, the CPU 1A, when a predetermined time elapses from execution of the last calibration processing, the oscillometric measuring section 20 is forcibly activated to perform measurement of a blood pressure in an oscillometric method and a calibration processing even in a case where a user selects a measurement mode according to an SPD method. Moreover, while no calibration information on a user as an individual is reflected in an algorithm of an SPD method immediately after purchase of an electronic blood pressure monitor by the user, in such a case as well, the CPU 1A recognizes whether or not the equipment is used for the first time and when a first time use is recognized, the oscillometric measuring section 20 is unconditionally activated, followed by measurement of a blood pressure according to an oscillometric method and a calibration processing.

Description will be given of measurement of a blood pressure according to an oscillometric method, a calibration processing included therein, and measurement of a blood pressure according to an SPD method in the order below.
(Operations in Measurement of a Blood Pressure According to Oscillometric Method)

Figure 3:
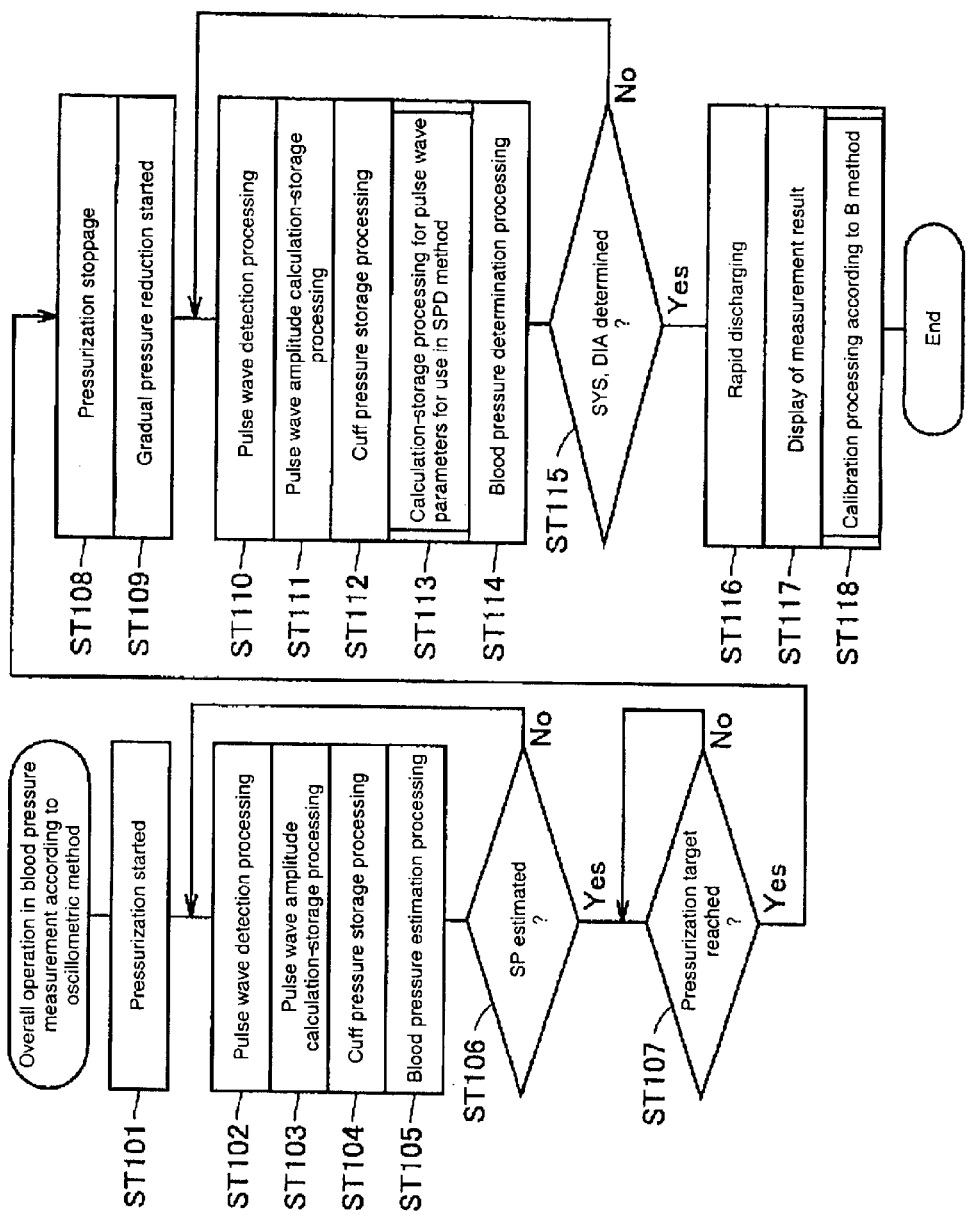
FIG. 3 is a flowchart showing an overall operation in blood pressure measurement according to an oscillometric method relating to the first embodiment.
Figure 4A:
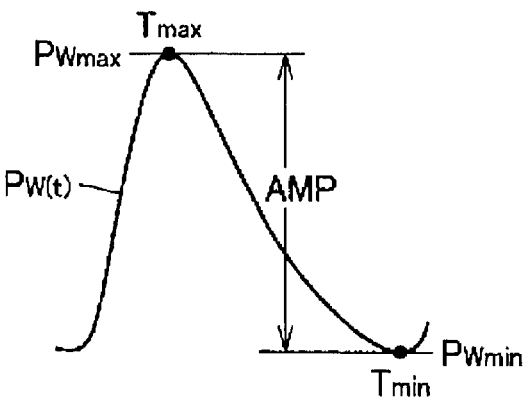
FIGS. 4A to 4D are graphs showing pulse wave parameters.
Figure 4B:
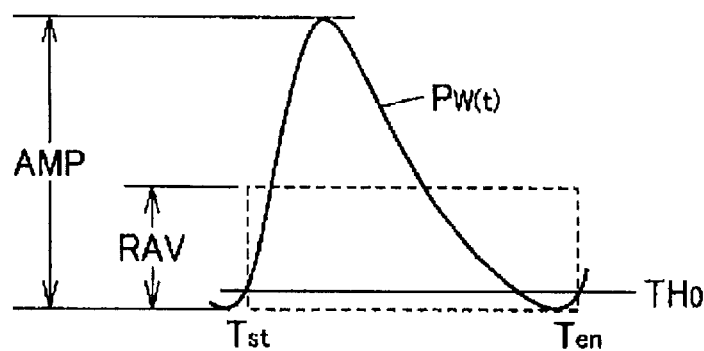
Figure 4C:
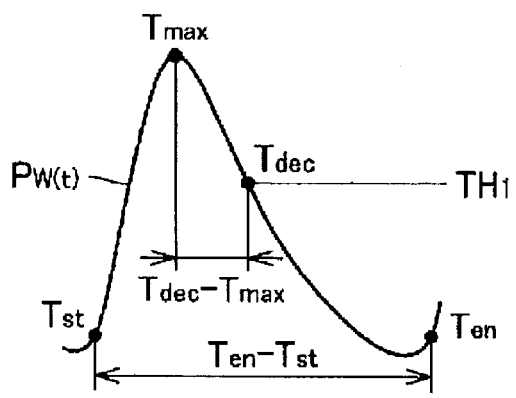
Figure 4D:
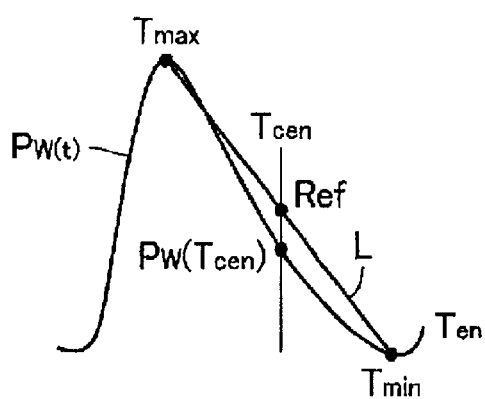

FIG. 3 is a flowchart showing an overall operation in blood pressure measurement according to an oscillometric method relating to this embodiment. A processing of FIG. 3 corresponds to the processing in ST2 of FIG. 2.

When an operation in measurement is activated by a switch operation or the like through the input interface 10 of a user, pressurization in the cuff 2 is started by the pressurizing section 5 (ST101). The pulse wave detecting section 7 recognizes each pulse wave during the pressurization (ST102) and when amplitude data of a pulse wave is calculated, the values are sequentially stored into the memory 1B (ST103). Furthermore, data of a cuff pressure corresponding to the recognized pulse wave is detected by the cuff pressure detecting section 6 to be related to amplitude data of the pulse wave and stored into the memory 1B (ST104).

Such detection and storage operation are repeated till a state is reached where contents of storage in the memory 1B can estimate a systolic blood pressure SP to be estimated. A systolic blood pressure SP is estimated based on cuff pressures and amplitude data of pulse waves stored and accumulated by this repetition (ST105). In a state where a systolic blood pressure SP cannot be still estimated (No in ST106), the process returns to ST102 and the processing between ST102 to ST105 is repeated till a state is reached where the systolic blood pressure SP can be estimated (Yes in ST106).

When it is determined that estimation of the systolic blood pressure SP has been completed (yes in ST106), it is further determined whether or not a current cuff pressure has reached a pressurization target value set based on a value of the systolic blood pressure SP (ST107) and when it is determined that a current cuff pressure has reached (Yes in ST107), pressurization in the cuff 2 performed by the pressurizing section 5 is stopped (ST108).

The above operations are those performed by the above automatic pressure setting function. Note that a systolic blood pressure SP estimated here is an estimated value obtained in the course during which pressurization progresses at high speed for performing pressure setting which is different from another estimated value finally determined as a measured value and displayed through the output interface 11.

After the stoppage of pressurization, a cuff pressure is gradually reduced by the gradual pressure reduction section 3 for the purpose to measure a blood pressure (ST109). A systolic blood pressure SYS and a diastolic blood pressure DIA are sequentially calculated and determined by a similar processing to that during pressurization using amplitudes of pulse waves and cuff pressures chronologically detected during reduction in pressure. The systolic blood pressure SYS and the diastolic blood pressure DIA are stored into the memory 1B. At this time, an average blood pressure may be determined (ST110 to ST114).

In a processing of ST113, various kinds of pulse parameters (a pulse wave characteristic amount) of a user is calculated by the data gathering section 23 and stored into the table TB of the memory 1B. Description will be given of details of the processing of ST113 later.

Thereafter, when it is determined that the systolic blood pressure SYS and the diastolic pressure DIA have been determined (Yes in ST115), the cuff pressure is completely removed by the rapid discharging section 4 and the systolic blood pressure SYS and the diastolic blood pressure DIA, which are results of measurement, are outputted as data through the output interface 11 (ST116 and ST117). Thereafter, a calibration processing is performed by the updating section 24 (ST118). In other words, in a SPD method, calculation is performed of a function (hereinafter referred to as a corrective function) applied for calibrating a precision of measurement for each individual and values of probability density functions FG in the memory 1B is updated using the corrective function. Thereafter, the operation in measurement of a blood pressure according to an oscillometric method ends. Description will be given of details of the processing of ST118 later.

(Principle of Measurement of Blood Pressure According to SPD Method)

Herein, a value showing by how much a current cuff pressure is higher or lower than a blood pressure (one of a systolic blood pressure SYS, a diastolic blood pressure DIA and an average blood pressure) is called a relative cuff pressure RPc.

FIGS. 4A to 4D are graphs showing pulse wave parameters. FIGS. 5A to 5D are graphs showing values of pulse wave parameters plotted using the abscissas on which a scale for a relative cuff pressure RPc is calibrated. FIG. 6 is a diagram illustrating a probability density function calculated from a probability density distribution.

A waveform of a pulse wave alters depending on a level of a relative cuff pressure RPc.

A principle of measurement of a SPD method is based on a relationship between a relative cuff pressure RPc and a change in waveform of a pulse wave (hereinafter referred to as a "relationship between a pressure and a waveform"). A pulse wave is captured by raising a cuff pressure to an arbitrary value and a waveform characteristic amount is compared with a relationship between a pressure and a waveform shown by a set of probability density functions FG stored in advance in the memory 1B to estimate a relative cuff pressure RPc at a time when a pulse wave is captured. Since a cuff pressure at a time when a pulse wave is captured (hereinafter referred to as an "absolute cuff pressure" Pc) can be easily known from the cuff pressure detecting section 6, a blood pressure can be estimated as a remainder obtained by subtracting a value of a relative cuff pressure RPc from an absolute cuff pressure Pc.

While waveform characteristics of a pulse wave can be thought in various ways, for example, 4 kinds of pulse wave parameters are calculated in order to quantify the waveform characteristics: such as a pulse wave amplitude AMP, a pulse wave integrated level RAV, a relative waveform width WID and a degree of curving CON as shown in FIGS. 4A to 4D. There has only to be available at least one or one kind of pulse wave parameter showing a waveform characteristic of a pulse wave, no specific limitation is placed to the above 4 kinds of characteristics. Since a procedure in which the pulse wave parameters are calculated is disclosed in JP patent No. 2745467 (U.S. Pat. No. 5,156,158 corresponding to the JP), description is here omitted of the calculating procedure and of the various kinds of variables in the figures. Values of the 4 kinds of pulse wave parameters were gathered from a great number of individuals in test in advance to plot them in a plane of a two-dimensional coordinate system with a relative cuff pressure RPc assigned to the abscissa; thereby obtaining distribution statuses as shown in FIGS. 5A to 5D.

It can be seen from the figures that a distribution region of values of a pulse wave parameter alters depending on a relative cuff pressure RPc. This shows that a pulse wave is actually measured to compare measured values of the pulse wave parameters with distributed values in the figures; thereby enabling estimation of a relative cuff pressure RPc to be in a limited range with some accuracy. In other words, distribution statuses as shown in FIGS. 5A to 5D can be each considered to be a probability density distribution of a relative cuff pressure RPc depending on a level of a pulse parameter (a value read using a scale on the ordinate). It is further understood from comparison between FIGS. 5A to 5D that a distribution region depending on a relative cuff pressure RPc is different according to a kind of a pulse parameter. This means that though a relative cuff pressure RPc cannot be specified within a sufficiently narrow range only with respect to a single individual pulse parameter, a combination of plural kinds of pule wave parameters having respective different distributions can specify a relative cuff pressure RPc within a narrower range.

Each of distribution information on the pulse wave parameters of FIGS. 5A to 5D is to be compared with measured values of the parameters of a pulse wave in a case where a blood pressure is measured in an SPD method and stored in a memory 1B or a memory, installed separately, and not shown, in advance. Though a distribution information of each of the pulse wave parameters maybe stored in the memory 1B in the format accompanied with an expression, a way of storage in the memory 1B can considered to save a memory capacity that a plane between a relative cuff pressure RPc (on the abscissa) and a level of a pulse wave parameter (on the ordinate) is two-dimensionally divided into ranks at a sufficiently small spacing in both directions and the distribution information of each of the pulse wave parameters is stored in the memory 1B in the format of a data table with the number of points included in each of the ranks as a value of a probability density function. Note that FIG. 6 is a data table constructed using data of FIG. 5B. Each of the data tables of the respective pulse wave parameters can be considered to be a set of plural probability density functions of parameter levels in a range. Herein, a set of functions are provided for each kind of pulse wave parameters and stored in the memory 1B as a set of probability density functions FG.

Then, description will be given of a processing when a blood pressure is actually measured by the SPD measuring section 30.

The cuff 2 is at first pressurized to an arbitrary pressure through the pressurizing section 5. A pressure value (an absolute cuff pressure Pc) in the case can be detected with ease by the cuff pressure detecting section 6. Then, at least one pulse wave is captured by the pulse wave detecting section 7 under the absolute cuff pressure Pc and values of kinds of pulse wave parameters of the captured pulse wave are calculated in the parameter measuring section 31. The values of the pulse wave parameters calculated with respect to the captured pulse wave are each called a measured value of a parameter. Then, the function selection section 32 selectively extracts a probability density function of a parameter level coinciding with the measured values of a parameter among a set of corresponding probability density functions FG for each of the kinds of pulse wave parameters.

A probability density function extracted in such a way is called a sub-probability density function.

When in this embodiment, sub-probability density functions are extracted with respect to the respective above 4 kinds of pulse wave parameters (a pulse wave amplitude AMP, a pulse wave integrated level RAV, a relative waveform width WID and a degree of curving CON), for example, as shown in FIGS. 7A to 7D, 4 sub-probability density functions Pamp, Prav, Pwid and Pcon are selectively extracted from respective sets of probability density functions FG. In other words, a probability density of a relative cuff pressure RPc based on distributions of values of the respective pulse wave parameters and measured values of the parameters is shown with 4 sub-probability density functions Pamp, Prav, Pwid and Pcon.

Figure 7A:
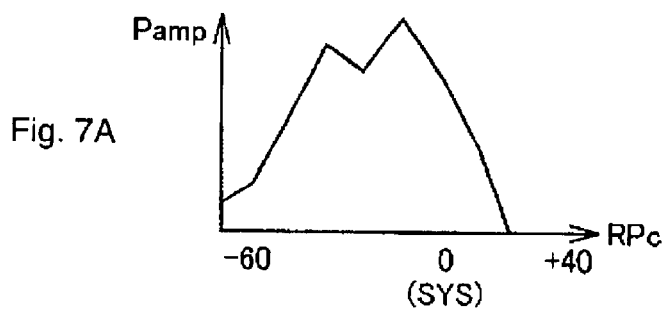
FIGS. 7A to 7E are graphs showing extracted probability density functions and an integrated probability density function.
Figure 7B:
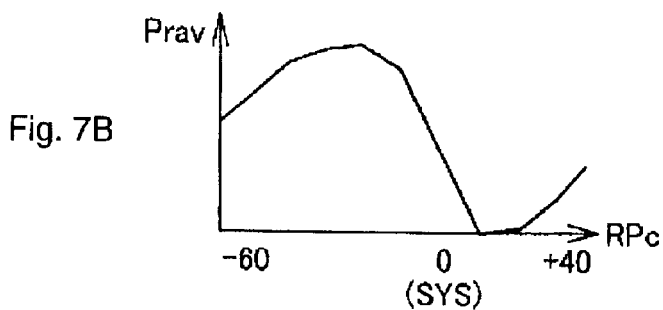
Figure 7C:
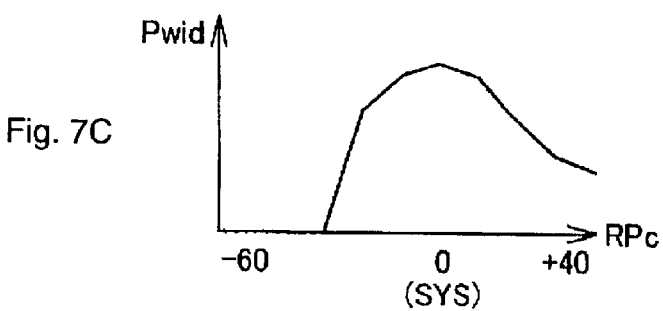
Figure 7D:
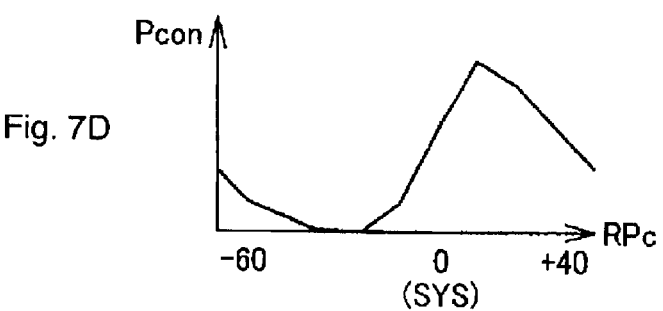
Figure 7E:
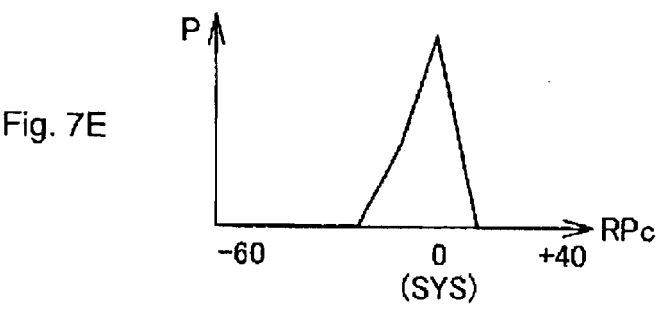

Sub-probability density functions of the pulse wave parameters, as shown in FIGS. 7A to 7D, do not coincide with each other. A necessity arises for integrating information of the sub-probability density functions to obtain one estimated value of a relative cuff pressure RPc in order to obtain a blood pressure. Therefore, the blood pressure calculating section 33 performs an operation such as multiplication or addition on values of different sub-probability density functions corresponding to the same level of a relative cuff pressure RPc therebetween. A result obtained in this way is one probability density function according to a relative cuff pressure RPc as shown in FIG. 7E. This is called a total probability density function P.

Since the total probability density function P integrates information of all the pulse parameters to show a relative cuff pressure RPc that can be produced at each level, a value of a relative cuff pressure RPc corresponding to the maximum value of the total probability density function P can be the most probable value, that is to say, an estimated value. The blood pressure calculating section 33 attains an estimated value of a blood pressure by subtracting the estimated value of a relative cuff pressure RPc from a value of an absolute cuff pressure Pc when a pulse wave is captured.

According to a SPD method, as described above, since a blood pressure can be estimated only by capturing one pulse wave in the principle, it has a feature that a time required for measurement can be greatly shortened compared with an oscillometric method.

An equipment construction of an electronic blood pressure monitor based on the principle of measurement of an SPD method may be altogether in common with that shown in FIG. 14. However, in a case where a cuff pressure is preferably constant during capturing of a pulse wave, a discharging valve of the gradual pressure reduction section 3 may also be completely shut off.

(Operations in Measurement of a Blood Pressure According to SPD Method According to This Embodiment)

Figure 8:
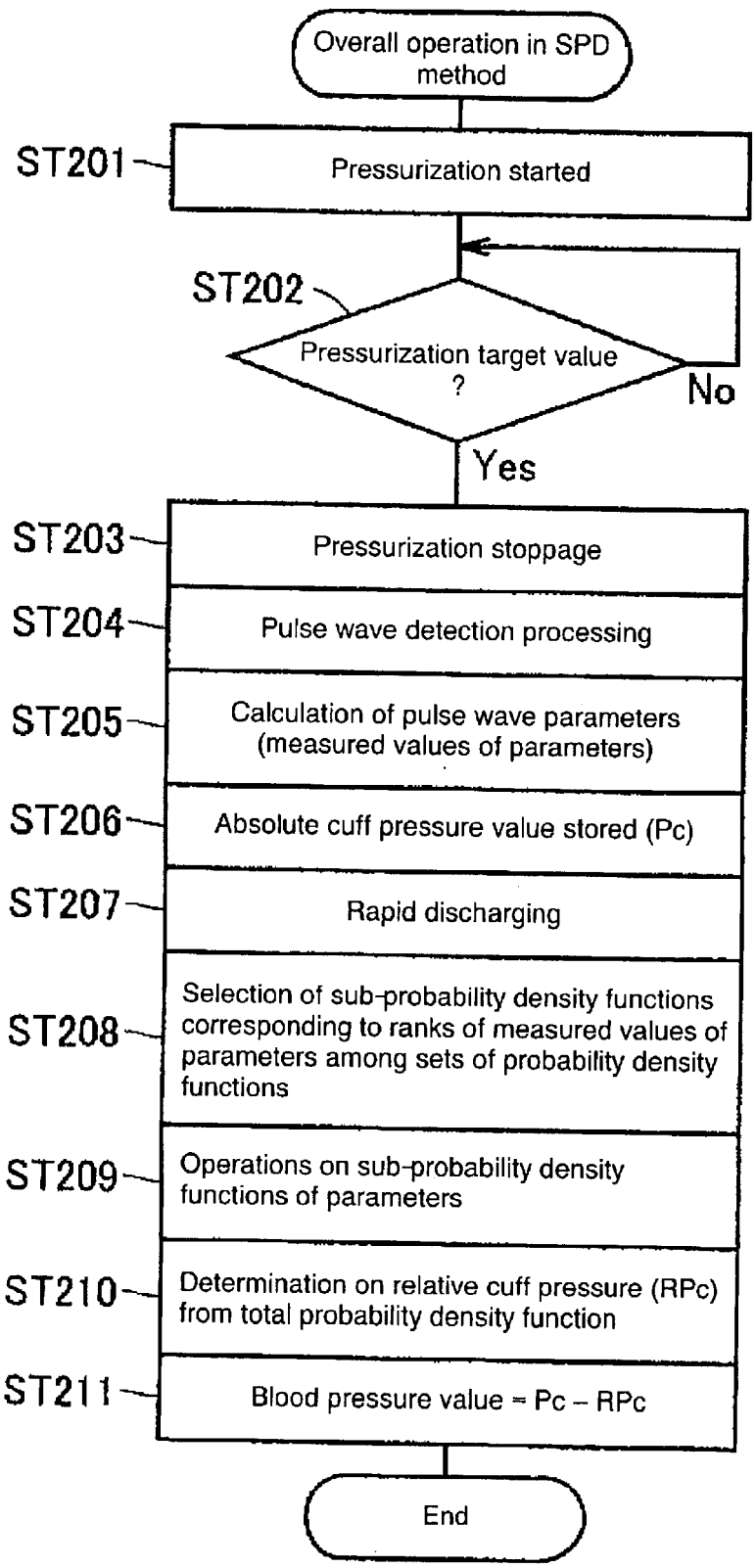
FIG. 8 is a flowchart for blood pressure measurement with an SPD method.

Description will be given of measurement of a blood pressure relating to this embodiment of a SPD method based on the principle of measurement as described above following a flowchart for measurement of a blood pressure according to an SPD method of FIG. 8. The flowchart of FIG. 8 corresponds to the processing of ST3 of FIG. 2.

When a user at first performs a switch operation of the input interface 10 to activate an operation in measurement of a blood pressure with the SPD measuring section 33, the pressurizing section 5 operates to start pressurization inside the cuff 2 (ST201), and when it is determined that a cuff pressure detected by the cuff pressure detecting section 6 has reached a predetermined pressurization target value (yes in ST202), the pressurization by the pressurizing section 5 is stopped (ST203).

At least one pule wave is detected by the pulse wave detecting section 7 (ST204) and calculations are performed to obtain values of 4 kinds of pulse wave parameters as described above, that is to say, measured values of parameters with respect to the at least one pulse (ST205). Then, an absolute cuff pressure Pc, which is a cuff pressure at a time when the pulse wave is detected is detected by the cuff pressure detecting section 6, a value of the absolute cuff pressure Pc is stored into the memory 1B (ST206) and the cuff pressure is rapidly reduced by the rapid discharging section 4 to be eventually removed (ST207).

Then, the function selection section 32 determines which of parameters ranks of a corresponding set of probability density functions FG stored in advance in the memory 1B a level of each of the obtained measured values of the 4 kinds of parameters corresponds to and selectively extracts corresponding probability density functions. That is to say, sub-probability density functions are extracted for the 4 kinds of respective measured parameters (ST208).

Then, the blood pressure calculating section 33 performs operations on the values of the sub-probability density functions selectively extracted with respect to the measured value of the respective parameters at a level of the corresponding relative cuff pressure RPc (ST209). This corresponds to the processing in which the sub-probability density functions Pamp, Prav, Pwid and Pcon shown in FIGS. 7A to 7D are subjected to operations (addition or multiplication) to attain a total probability density function P (see FIG. 7E).

Then, determination is performed on a value of the relative cuff pressure RPc imparting the maximum value to the total probability density function P (ST210). Finally, an estimated value of the relative cuff pressure RPc is subtracted from a value of the absolute cuff pressure Pc to output a result of the operation as an estimated value of blood pressure (at least one of a systolic blood pressure, a diastolic blood pressure and an average blood pressure) (ST211).

Note that while, in the above description, a systolic blood pressure and a diastolic blood pressure are collectively called a blood pressure, a systolic blood pressure and a diastolic blood pressure are in common in all of the process for calculation. In a case where each of systolic and diastolic pressures is calculated, kinds and the number of measured parameters and probability density functions may be different according to a kind of pressure since kinds of pulse wave parameters to be obtained with a high precision are not always the same.

Then, description will be given of processing for combining a blood pressure measuring function of an SPD method with that of an oscillometric method in effective use and operations in measurement with an electronic blood pressure monitor based on this embodiment.

Description will be given at first of a calibration processing for improvement on a precision of measurement with an SPD method (see S113 and S118 of FIG. 3). An SPD method uses a relationship between each of plural kinds of pulse wave parameters and a relative cuff pressure RPc obtained from a great number of individuals in test to estimate a blood pressure. There is, however, an individual difference in a relationship between a pressure and a waveform. Therefore, a necessity arises for causing a relationship between a pressure and a waveform for a particular individual to be reflected in a process for calculation of a blood pressure in order to improve a precision of measurement in an SPD method.

(Calibration Processing for Individual in SPD Method)

A processing for capturing calibration information for each individual in ST113 of FIG. 3 is repeated in each detection of a pulse wave till a blood pressure (a systolic blood pressure SYS and a diastolic blood pressure DIA) is determined. Therefore, the data gathering section 23 provides, for each pulse wave, measured values of the 4 kinds of parameters through calculation, detects an absolute cuff pressure Pc corresponding to the pulse wave and stores, for each pulse wave, the provided measured values and the detected value, being related with each other, onto the table TB of the memory 1B.

FIGS. 9A and 9B are representations showing tables TB filled out with values of 4 kinds of pulse wave parameters and corresponding values of an absolute cuff pressure Pc for each of pulse waves. In the table TB of FIG. 9A, there are registered measured values P1 (i) to P4 (i) of the 4 kinds of parameters through calculation related with a value Pc (i) of detected absolute cuff pressures Pc, also registered there, for the ith pulse wave, where i=1,2 3, . . . , N.

Then, it is considered to cause data of pulse wave parameters, which is calibration information for the table TB, to be reflected in probability density functions as shown in FIG. 6. Pulse wave parameters of an individual as are cannot be related to probability density functions. This is because probability density functions are defined as functions of a relative cuff pressure RPc; therefore, a value of a probability density function given in each regular rank at a particular pair of a relative cuff pressure RPc and a parameter level, whereas data of pulse wave parameters of an individual registered in the table TB of FIG. 9A assumes the format of irregular discrete data corresponding to each absolute cuff pressure Pc.

Therefore, in this embodiment, when calibration information for an individual is acquired in the table TB, a calibration processing in a SPD method of FIG. 3 is performed (ST118). To be concrete, the data gathering section 23 causes data of pulse wave parameters of an individual to be related with a relative cuff pressure RPc. In other words, values of relative cuff pressures RPc(1), RPc(2), . . . , RPc(N) are obtained by subtracting a value of a systolic blood pressure SYS, a diastolic blood pressure DIA or an average blood pressure, which are stored in the memory 1B after being determined in ST114 of FIG. 3, from values of absolute cuff pressure Pc(1), Pc(2), . . . , Pc(N) in the table TB of FIG. 9A. For example, in a case of the subtraction with a value of systolic blood pressure SYS, the values of relative cuff pressures RPc(1), RPc(2), . . . , RPc (N) are obtained in such a manner that RPc(1)=Pc(1)−SYS, RPc(2)=Pc(2)−SYS, . . . , RPc(N)=Pc(N)−SYS.

As a result, a calculated value RPc(i) of a relative cuff pressure RPc is additionally registered in the table TB, which is transformed into that of FIG. 9B.

The updating section 24 causes irregular discrete data of pulse wave parameters of an individual to be reflected in probability density functions. Description will be given of this processing.

Figure 10:
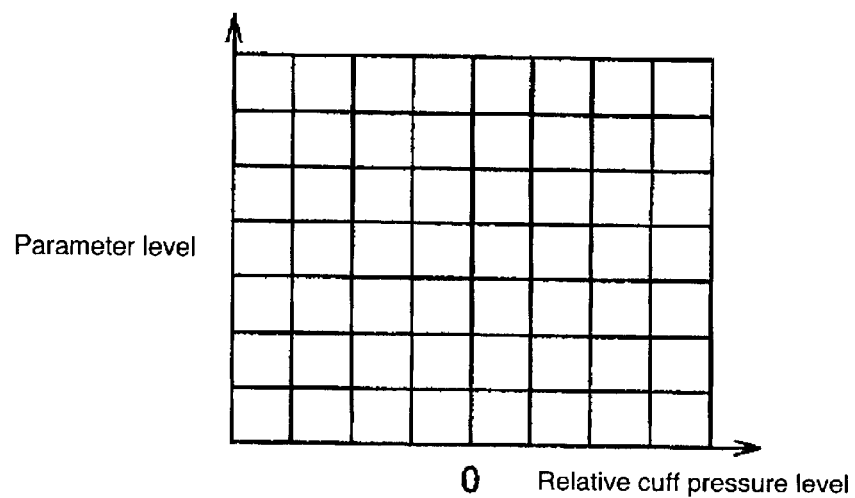
FIG. 10 is a graph showing ranks formed in a plane of a coordinate system using a scale for a relative cuff pressure calibrated on the abscissa and a scale for a parameter level calibrated on the ordinate.
Figure 11:
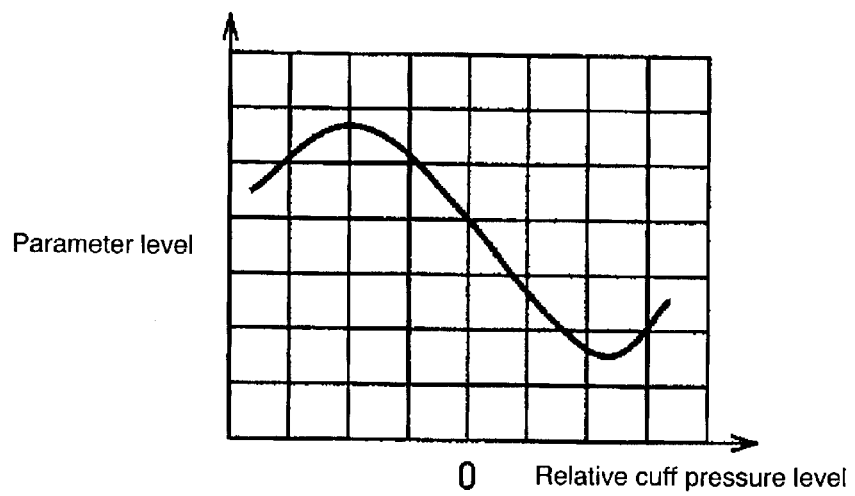
FIG. 11 is a graph showing a curve formed by parameter data of an individual plotted on the coordinate system with ranks.

FIG. 10 shows a state of a graph in which levels of a value RPc(i) of a relative cuff pressure RPc and each of pulse wave parameters P1(i) to P4(i) are divided into the same ranks in lattice as in the set of probability density functions registered in the memory 1B in advance. When data of a kind of pulse wave parameter Pj(i) (j=1, 2, 3 and 4) of an individual of FIG. 9B described above is plotted using the coordinate system with divided ranks arranged in lattice, a curve obtained by the plotting passes through part of the lattice cells as shown in FIG. 11. In other words, it can be said that this user has a low probability to provide a relationship between a pressure and a waveform in regions other than the part of the lattice cells.

Figure 12:
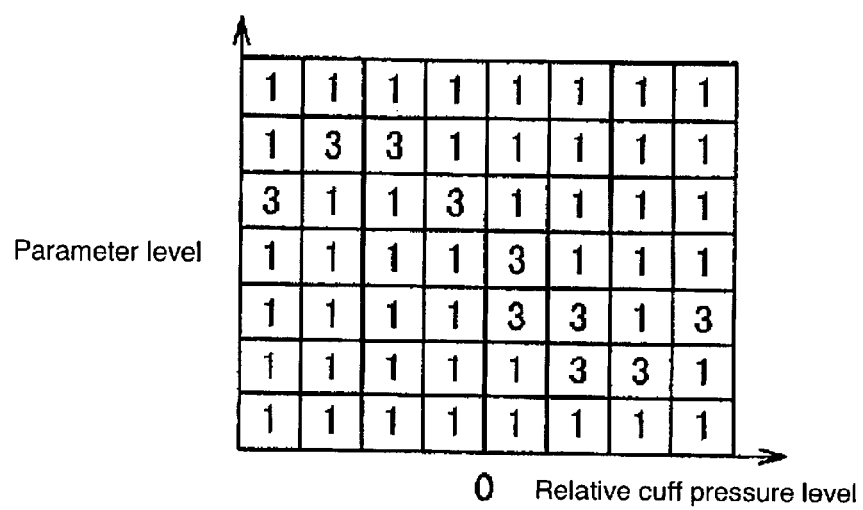
FIG. 12 is a graph showing parameter data of an individual filled in regularly patterned ranks.

Then, a corrective function is obtained that is used for correcting a set of probability density functions FG so as to be closer to the relationship between a pressure and a waveform of this individual. To be concrete, as shown in FIG. 12, a function is at first provided that has initial values of, for example, 1 or the like in all the ranks arranged in lattice. Then, values of the function only in the ranks through which the curve of FIG. 11 passes are altered to values larger than the initial ones, for example 3 to obtain the corrective function. At the final stage, values of each of the set of probability density functions FG corresponding to ranks are multiplied by respective values (1 or 3) of the ranks of the corrective function. As a result of the multiplication, in the set of probability density functions FG, a probability density function assume relatively larger values in a region in which the relationship between a pressure and a waveform for the individual is produced; thereby enabling increase in precision of an estimated value since data of an individual is reflected in the course of estimation of a blood pressure with an SPD method.

Note that while multiplication is herein used in an operation using the corrective function and a probability density function, no specific limitation is placed to multiplication, but for example, addition may be used as the operation instead.

Furthermore, while the 4 kinds of parameters are required as measured values thereof, at least one kind of parameter will be sufficient.

(Second Embodiment)

Calculation of a blood pressure is enabled at an arbitrary level of a cuff pressure in the principle according to an SPD method, whereas if a level of a cuff pressure level is excessively apart from an actual blood pressure level, an amplitude of a pule wave becomes small to reduce an S/N ratio and thereby a probability density function does not give a correct estimated value of blood pressure to deteriorate a precision of calculation of a blood pressure. Therefore, in the second embodiment, an automatic pressure setting function of the pressure set up section 34 is applied to the blood pressure measuring function according to an SPD method of the first embodiment to optimize a pressurization value in the SPD method and to, as a result, obtain a higher precision of measurement.

(Optimization of Pressure Setting in SPD Method)

Figure 13:
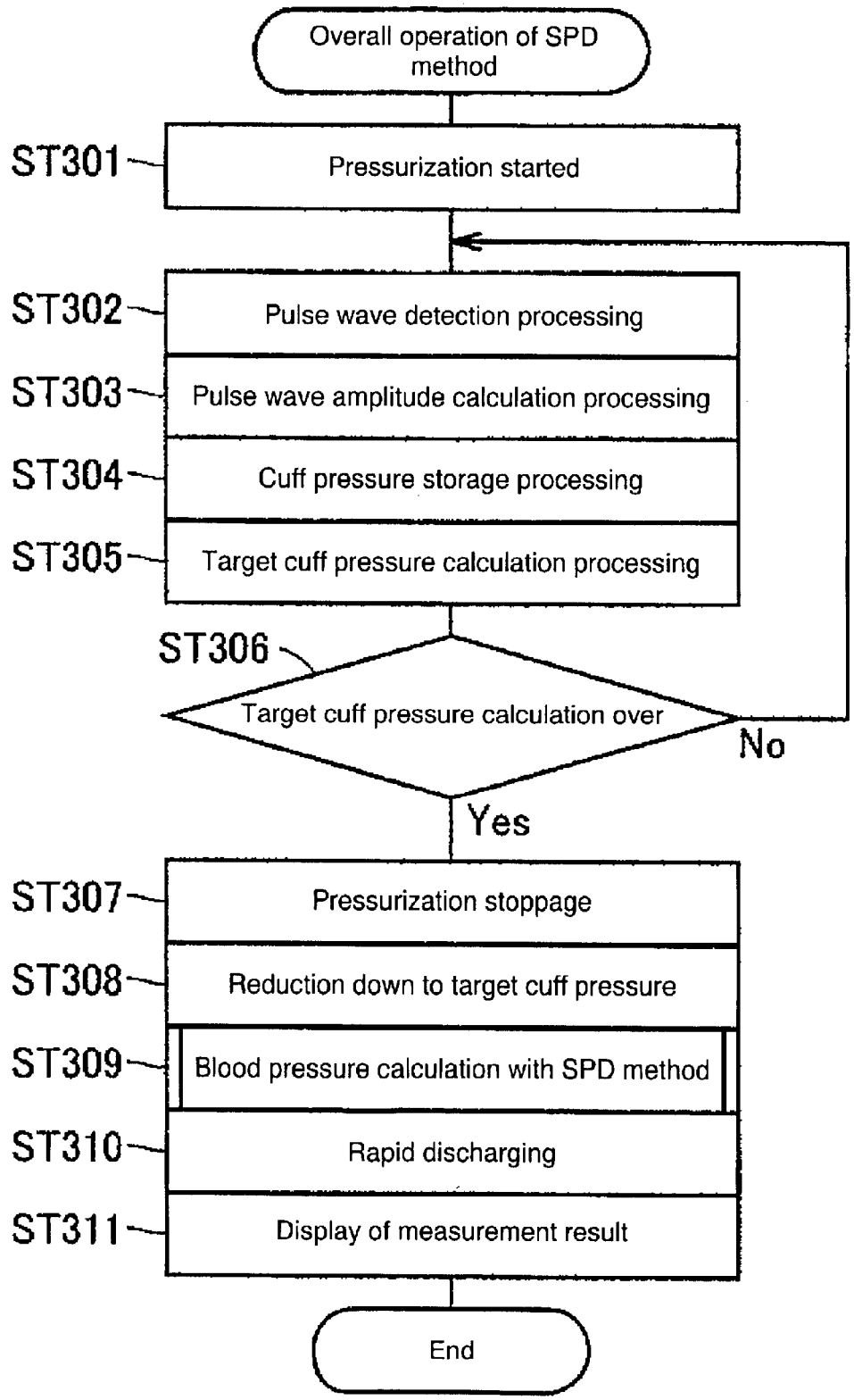
FIG. 13 is a flowchart for an overall operation in an SPD method added with a pressure setting optimization function.

In FIG. 13, there is shown a flowchart for an overall operation in blood pressure measurement with an SPD method in the second embodiment. When a user performs a switch operation of the input interface 10 and an operation in blood pressure measurement is activated by the SPD blood pressure measuring section 30, pressurization is started in the cuff 2 by the pressurizing section 5 (ST301). Then, detection of a pulse wave is started by the pule wave detecting section 7 to give a detected pulse wave data to the microprocessor 1; therefore, the CPU 1A sequentially calculates amplitude data of a given pulse wave to store the data into the memory 1B (ST302 and ST303). At this time, since a corresponding absolute cuff pressure Pc is simultaneously detected by the cuff pressure detecting section 6 and given to the microprocessor 1, data of the absolute cuff pressure Pc is similarly related with amplitude data of the pusle wave to be sequentially stored into the memory 1B (ST304).

Then, pressurization is performed up to a target cuff pressure value in order to perform blood pressure measurement with an SPD method and the target cuff pressure value is calculated based on contents of the memory 1B (ST305).

As to a procedure for the calculation, various ways can be applied according to what value a target cuff pressure value is set to. For example, if one of a systolic blood pressure SYS and a diastolic blood pressure DIA is thought more than the other and desired to be calculated with more of a precision, an estimation processing of a blood pressure similar to an oscillometric method has only to be performed using data of an amplitude of a pulse wave and a cuff pressure Pc calculated and stored in ST303 and ST304 to obtain an estimated value of one of a systolic blood pressure and a diastolic blood pressure and to adopt the estimated value as a target cuff pressure value. Furthermore, it is also allowed to obtain an estimated value of an average blood pressure value and to adopt the estimated value as a target cuff pressure value. If a characteristic amount of a waveform of pulse wave is desired to be calculated with a good precision, it is recommended that a cuff pressure Pc value that has the maximum amplitude of a pule wave is detected to adopt the cuff pressure Pc value as a target cuff pressure value. Moreover, a value may be adopted that is calculated from a combination of at least two of estimated values of a systolic blood pressure, a diastolic blood pressure and an average blood pressure, and a cuff pressure Pc value at which a pulse wave takes the maximum amplitude value.

In any way, when a target cuff pressure value is calculated in ST305, it is determined in ST306 whether or not the calculation is over and a processing from ST302 to ST305 is repeated as long as it is not determined that the calculation is over. If it is determined that the calculation is over (Yes in ST306), pressurization in the cuff 2 of the pressurizing section 5 is stopped. (ST307) and if a target cuff pressure value is lower than a current cuff pressure Pc, the cuff pressure Pc is reduced by the rapid pressure reduction section 4 till the cuff pressure is rendered to be a target cuff pressure value (ST308).

Then, a result of a blood pressure measurement is obtained (ST309) by performing an SPD blood pressure measuring processing to which a calibration processing according to the first embodiment (ST204 to ST211) is applied. Thereafter, a cuff pressure is completely removed by the rapid discharging section 4 (ST310) to output the result of the measurement through the output interface 11 and to thereby terminate the operation.

In the second embodiment, since automatic pressure setting function is applied to a blood pressure measuring function according to an SPD method of the first embodiment to optimize a pressurization value of the SPD method, a higher precision of measurement can be obtained.

It should be understood that the embodiments disclosed herein are presented by way of illustration but not by way of limitation at all respects. It is intended that the scope of the present invention is not shown by the above description of the specification but by the scope of the claims, and includes all modifications or alterations thereof within the scope of the claims and ones equivalent thereto.

What is claimed is:

1. An electronic blood pressure monitor comprising:
   a cuff configured to be mounted on a predetermined portion of a subject for pressurizing an artery of the subject;
   a cuff pressure controller for controlling a cuff pressure inside the cuff;
   a pressure detector for detecting the cuff pressure;
   a pulse wave detector for detecting a pulse wave of the artery that is pressurized by the cuff; and
   a first blood pressure measuring portion and a second blood pressure measuring portion, the electronic blood pressure monitor selectively using the first or second blood pressure measuring portion at a time, wherein
   the first blood pressure measuring portion comprises a first calculating unit that calculates a blood pressure of the subject based on a set of the cuff pressures chronologically detected by the pressure detector during a period in which the cuff pressure is gradually changed by the cuff pressure controller and on amplitudes of the pulse waves detected by the pulse wave detector at the timings of the corresponding cuff pressure detection by the pressure detector, and a calibration unit that calibrates the second blood pressure measuring portion based on a result of the blood pressure calculation by the first calculating unit, and
   the second blood pressure measuring portion comprises a parameter measuring unit that provides a measured value of a pulse wave parameter based on at least one of the pulse waves detected by the pulse wave detector, the pulse wave parameter being indicative of a waveform of the pulse wave that represents a relative cuff pressure corresponding to a pressure difference between the detected cuff pressure and the blood pressure of the subject, a function memory that stores a function of the relative cuff pressure comprising a set of sub-functions, a function selection unit that selects one of the sub-functions that corresponds to a level of the measured value of the pulse wave parameter, and a second calculating unit that identifies the relative cuff pressure based on the selected sub-function and calculates the blood pressure of the subject by subtracting the identified relative cuff pressure from the cuff pressure detected by the pressure detector at the time of the pulse wave detection, wherein
   the calibration unit comprises a data gathering unit that gathers, for each of the pulse waves detected during an operation of the first blood pressure measuring portion at the timings of the corresponding cuff pressure detection, the corresponding relative cuff pressure and the corresponding measured value of the pulse wave parameter, and a data updating unit that modifies the function based on the relative cuff pressures and the corresponding measured values of the pulse wave parameter that are gathered by data gathering unit.

2. The electronic blood pressure monitor of claim 1, wherein during the operation of the second blood pressure measuring portion the parameter measuring unit provides a measured value of at least one more pulse wave parameter, the function memory stores a plurality of the functions for the corresponding pulse wave parameters, the function selection units selects one of the sub-functions for each of the pulse wave parameters, and the second calculating unit generates a total function that provides a probability as a function of the relative cuff pressure and determines the relative cuff pressure for the calculation of the blood pressure as providing a maximum probability.

3. The electronic blood pressure monitor of claim 2, wherein the data gathering unit gathers the relative cuff pressures and the measured values for each of the pulse wave parameters, and the data updating unit modifies the corresponding function for each of the pulse wave parameters.

4. The electronic blood pressure monitor of claim 1, further comprising an input interface that allows an external data input, wherein the first or second blood pressure measuring portion is selected by the electronic blood pressure monitor based on the external data input.

5. The electronic blood pressure monitor of claim 1, wherein the data gathering unit determines the relative cuff pressures based on the cuff pressures and a measured blood pressure as a result of the operation of the first blood pressure measuring portion.

6. The electronic blood pressure monitor of claim 1, wherein the second blood pressure measuring portion further comprises a pressure setup unit that calculates a target pressure based on the cuff pressures detected by the pressure detector while the cuff pressure is increased by the cuff pressure controller and on the amplitudes of the pulse waves detected by the pulse wave detector at the timings of the cuff pressure detection during the cuff pressure increase and increases the cuff pressure to the target pressure using the cuff pressure controller, the target pressure being enough to assure an accurate blood pressure measurement by the second blood pressure measurement portion, wherein the pulse wave detected for providing the measured value of the pulse wave parameter is detected when or after the cuff pressure reaches the target pressure.

7. The electronic blood pressure monitor of claim 6, the target pressure is one of or a combination of a systolic blood pressure, a diastolic blood pressure, an average blood pressure and a cuff pressure to provide an maximum amplitude of the pulse wave.

8. An electronic blood pressure monitor comprising:

a cuff configured to be mounted on a predetermined portion of a subject for pressurizing an artery of the subject;

a cuff pressure controller for controlling a cuff pressure inside the cuff;

a pressure detector for detecting the cuff pressure;

a pulse wave detector for detecting a pulse wave of the artery that is pressurized by the cuff; and a first blood pressure measuring portion comprising a first calculating unit that calculates a blood pressure of the subject based on a set of the cuff pressures chronologically detected by the pressure detector during a period in which the cuff pressure is gradually changed by the cuff pressure controller and on amplitudes of the pulse waves detected by the pulse wave detector at the timings of the corresponding cuff pressure detection by the pressure detector, and a second blood pressure measuring portion comprising a parameter measuring unit that provides a measured value of a pulse wave parameter based on at least one of the pulse waves detected by the pulse wave detector, the pulse wave parameter being indicative of a waveform of the pulse wave that represents a relative cuff pressure corresponding to a pressure difference between the detected cuff pressure and the blood pressure of the subject, a function memory that stores a function of the relative cuff pressure comprising a set of sub-functions, a function selection unit that selects one of the sub-functions that corresponds to a level of the measured value of the pulse wave parameter, and a second calculating unit that identifies the relative cuff pressure based on the selected sub-function and calculates the blood pressure of the subject by subtracting the identified relative cuff pressure from the cuff pressure detected by the pressure detector at the time of the pulse wave detection, wherein the electronic blood pressure monitor selectively uses the first or second blood pressure measuring portion at a time.

9. The electronic blood pressure monitor of claim 8, wherein during the operation of the second blood pressure measuring portion the parameter measuring unit provides a measured value of at least one more pulse wave parameter, the function memory stores a plurality of the functions for the corresponding pulse wave parameters, the function selection units selects one of the sub-functions for each of the pulse wave parameters, and the second calculating unit generates a total function that provides a probability as a function of the relative cuff pressure and determines the relative cuff pressure for the calculation of the blood pressure as providing a maximum probability.

10. The electronic blood pressure monitor of claim 8, further comprising an input interface that allows an external data input, wherein the first or second blood pressure measuring portion is selected by the electronic blood pressure monitor based on the external data input.

* * * * *